United States Patent [19]

Ehrhardt et al.

[11] Patent Number: 4,495,191
[45] Date of Patent: Jan. 22, 1985

[54] FUNGICIDAL 3-1,2,4-TRIAZOL-1-YL-1,2-DIARYL-1-HALOGENO-PROP-1-ENE DERIVATIVES, COMPOSITIONS, AND METHOD OF USE

[75] Inventors: Heinz Ehrhardt, Rehling; Hilmar Mildenberger, Kelkheim; Burkhard Sachse, Kelkheim; Peter Hartz, Kelkheim, all of Fed. Rep. of Germany

[73] Assignee: Hoechst Aktiengesellschaft, Frankfurt am Main, Fed. Rep. of Germany

[21] Appl. No.: 477,080

[22] Filed: Mar. 21, 1983

[30] Foreign Application Priority Data

Mar. 23, 1982 [DE] Fed. Rep. of Germany ....... 3210570

[51] Int. Cl.$^3$ ...................... C07D 249/08; A01N 9/22
[52] U.S. Cl. ..................................... 514/383; 548/262
[58] Field of Search ............................ 71/92; 424/269; 548/262, 265, 341, 378

[56] References Cited

U.S. PATENT DOCUMENTS 4,285,722  8/1981  Worthington et al. ................. 71/92

FOREIGN PATENT DOCUMENTS 2103119  7/1972  France ................................. 424/269
2652313  5/1978  France ................................. 424/269

Primary Examiner—Henry R. Jiles
Assistant Examiner—J. G. Mullins
Attorney, Agent, or Firm—Curtis, Morris & Safford

[57] ABSTRACT

Fungicidal 3-azolyl-1,2-diaryl-1-haloprop-1-enes of the formula

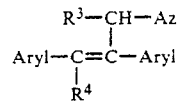

in which $R_4$ is chlorine or bromine, and Az is a 1,2,4-triazol-1-yl radical, and their preparation.

6 Claims, No Drawings

FUNGICIDAL 3-1,2,4-TRIAZOL-1-YL-1,2-DIARYL-1-HALOGENO-PROP-1-ENE DERIVATIVES, COMPOSITIONS, AND METHOD OF USE

It is known that 1,2-diaryl-3-triazolylprop-1-enes possess fungicidal properties (German Offenlegungsschrift No. 2,652,313). However, for their use in practice, it has proved disadvantageous that when lower amounts are used their activity against rust fungi and powdery mildew fungi is inadequate and their range of action is too narrow.

It has been found that 1,2-diaryl-3-azolylpropenes in which carbon atom 1 of the propene chain carries a halogen atom, and which are hence called 3-azolyl-1,2-diaryl-1-halogenoprop-1-enes, surprisingly possess substantially higher fungicidal against rust fungi and powdery mildew fungi than the abovementioned compounds, and at the same time combat a number of other fungal diseases in an outstanding manner.

The present invention therefore relates to 3-azolyl-1,2-diaryl-1-halogenoprop-1-enes which were hitherto unknown, of the formula (I)

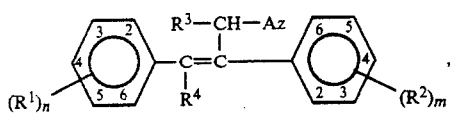

wherein $R^1$ and $R^2$ independently of one another represent hydrogen, halogen, $-CF_3$, $-OCF_2CF_2H$, $C_1-C_8$-alkyl, preferably $C_1$- or $C_2$-alkyl, $C_5$- or $C_6$-cycloalkyl, $C_1-C_6$-alkoxy, preferably $C_1$- or $C_2$-alkoxy, $C_2-C_6$-alkenoxy, preferably $C_3$-alkenoxy, phenoxy or phenyl, or the halogen substitution products of the two last-mentioned radicals, preferably those with 1 or 2 Br or Cl atoms, or denote radicals of the formulae $-CH_2CH_2CH_2-$, $-CH_2CH_2CH_2CH_2-$ and $-CH=CH-CH=CH-$, which link together the carbon atoms of ring positions 2 and 3 or 3 and 4. $R^1$ is preferably hydrogen or halogen, and $R^2$ is preferably halogen and/or trifluoromethyl, $R^3$ is hydrogen or a $C_1-C_5$-alkyl radical, preferably hydrogen, and $R^4$ represents chlorine or bromine, preferably chlorine.

n and m represent 1, 2 or 3, preferably 1 or 2, and in the case of polysubstitution, the substituents can also be different.

Az has the meaning 1,2,4-triazol-1-yl, imidazol-1-yl or pyrazol-1-yl.

It is also intended to include the salts, complex salts and quaternization products of the new compounds.

The invention furthermore relates to a process for the preparation of the 3-azolyl-1,2-diaryl-1-halogenoprop-1-enes and their use as biocides.

The new compounds are obtained by a process wherein 1 mole of 1,2-diaryl-1,3-dihalogenoprop-1-ene of the general formula (II), in which Hal is chlorine or bromine,

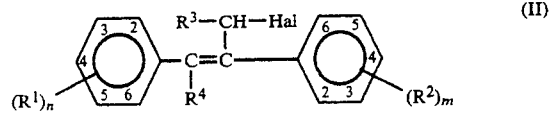

is reacted with 1 to 1.2 moles of 1,2,4-triazole, imidazole or pyrazole in the presence of a solvent and of a base as the hydrogen halide acceptor, at temperatures between 0° and 120° C., preferably between 25° and 80° C.

Suitable solvents are, preferably, aprotic dipolar ones, such as, for example, acetonitrile, dimethylformamide, dimethylsulfoxide and tetramethylenesulfone; acetonitrile and dimethylformamide are to be particularly recommended.

Excess azole, an alkali metal hydroxide, alkaline earth metal hydroxide, alkal metal carbonate or alkaline earth metal carbonate or a tertiary amine can be used as a base. Potassium carbonate is preferred. The base must be employed in at least a molar amount, based on the compound (II).

Some of the starting compounds of the formula (II), in particular those in which Hal is bromine, have been disclosed in German Offenlegungsschrift No. 2,103,119. These and also those which have not been described hitherto are prepared by the process given in that Offenlegungsschrift. Starting compounds of the formula (II), in which Hal is chlorine, are obtained by reacting the corresponding alcohols with 1.0 to 1.5 times the molar amount of thionyl chloride at 0° to 80° C., and the reaction can be carried out in the presence of diluents, such as, for example, carbon tetrachloride, and/or in the presence of pyridine in 1 to 10 times the amount by weight relative to the alcohol.

Examples of starting compounds of the formula (II) are: 1,3-dichloro-1,2-diphenylprop-1-ene, 1-bromo-3-chloro-1,2-diphenylprop-1-ene, 1-chloro-3-bromo-1,2-diphenylprop-1-ene, 1,3-dichloro-1,2-diphenylbut-1-ene, 1,3-dichloro-1-(4-methylphenyl)-2-phenylprop-1-ene, 1-(4-chlorophenyl)-1,3-dichloro-2-phenylprop-1-ene, 2-(2-chlorophenyl)-1,3-dichloro-1-phenylprop-1-ene, 2-(3-chlorophenyl)-1,3-dichloro-1-phenylprop-1-ene, 2-(4-chlorophenyl)-1,3-dichloro-1-phenylprop-1-ene, 2-(2-bromo-4-chlorophenyl)-1,3-dichloro-1-phenylprop-1-ene, 2-(4-bromo-2-chlorophenyl)-1,3-dichloro-1-phenylprop-1-ene, 1,3-dichloro-2-(2,4-dichlorophenyl)-1-phenylprop-1-ene, 1,3-dichloro-2-(2,4-dichlorophenyl)-1-(4-chlorophenyl)-prop-1-ene and 1,3-dichloro-2-(3,4-dichlorophenyl)-1-phenylprop-1-ene.

The new compounds, which in general are obtained in very good yield and with a high degree of purity, are isolated by customary methods, and any further purification which may be desired is carried out by distillation, crystallization or via salts.

The course of the reaction is surprising and could not be foreseen, since it was to be expected that both halogen atoms of the 1,2-diaryl-1,3-dihalogenoprop-1-ene of the formula (II) used as a starting material would react, in particular when these are bromine atoms, or $R^4$ is bromine and Hal is chlorine; the course of the reaction may be represented for the reaction of E-1,3-dichloro-1,2-diphenylprop-1-ene with 1,2,4-triazole:

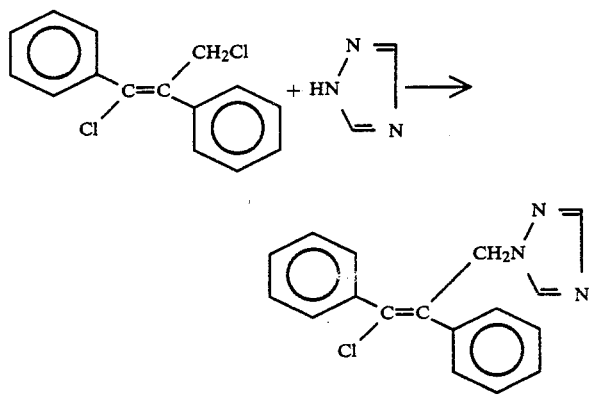

The new 3-azolyl-1,2-diaryl-1-halogenoprop-1-enes, which occur as E- and Z-isomers, preferably the former, and are synthesized, are basic compounds and hence capable of forming salts, complex salts and quaternization products. Salts of organic and inorganic acids, such as acetates, fumarates, oxalates, benzoates, etc., nitrates, bromides, chlorides and sulfates, salts of naphthalenesulfonic acids, complexes with metals of groups Ib, IIb, Ivb or VIII of the periodic table, for example, copper, zinc and tin, and quaternization products with alkyl and phenacyl halides may be mentioned. Such derivatives are prepared by the generally customary methods.

As already mentioned, the new compounds are distinguished, in particular, by their outstanding fungicidal activity. Even fungal pathogens which have already penetrated the plant tissue can be successfully combated curatively. This is particularly important and advantageous in the case of those fungal diseases which, once infection has occurred, can no longer be effectively combated with the fungicides otherwise customarily used. The spectrum of action of the new compounds furthermore includes a large number of diverse phytopathogenic fungi, such as, for example, *Piricularia oryzae*, *Plasmopara viticola*, various rust species, especially Venturia inaequalis, Cercospora beticola and powdery mildew fungi in fruit cultivation, vegetable cultivation, cereal cultivation and the cultivation of ornamental plants.

The agents can be used in the conventional formulations, as wettable powders, emulsifiable concentrates, atomizable solutions, dusting agents, dressing agents, dispersions, granules or microgranules.

Wettable powders are understood as meaning preparations which are uniformly dispersible in water and which contain, in addition to the active compound and if appropriate a diluent or inert substance, wetting agents, for example polyoxyethylated alkylphenols, polyoxyethylated fatty alcohols, alkylsulfonates or alkylphenylsulfonates, and dispersants, for example, sodium ligninsulfonate, sodium 2,2'-dinaphthylmethane-6,6'-disulfonate, sodium dibutylnaphthalenesulfonate or sodium oleoylmethyltaurinate. They are prepared in a conventional manner, for example by milling and mixing the components.

Emulsifiable concentrates can be prepared, for example, by dissolving the active compound in an inert organic solvent, for example butanol, cyclohexanone, dimethylformamide, xylene or higher-boiling aromatics or hydrocarbons, with the addition of one or more emulsifiers. In the case of liquid active compounds, a part or all of the solvent may be dispensed with. The following are examples of compounds which can be used as emulsifiers: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylenesorbitan fatty acid esters or polyoxyethylene sorbitol esters.

Dusting agents are obtained by milling the active compound with finely divided, solid substances, for example talc, natural clays, such as kaolin, bentonite or pyrophillite, or diatomaceous earth.

Granules can be produced either by atomizing the active compound onto adsorptive, granulated inert material, or by applying active compound concentrations by means of binders, for example polyvinyl alcohol, sodium polyacrylate or mineral oils, onto the surface of carriers, such as sand, kaolinite, or granulated inert material. It is also possible to granulate suitable active compounds in the manner conventionally used for the production of fertiliser granules—if desired, as a mixture with fertilisers.

In wettable powders, the active compound concentration is, for example, about 10 to 90% by weight, and the remainder, to make up to 100% by weight, consists of conventional formulation constituents. In the case of emulsifiable concentrates, the active compound concentration can be about 10 to 80% by weight. Dust-like formulations contain at least 5 to 20% by weight of active compound, and atomizable solutions contain about 1 to 20% by weight. In the case of granules, the active compound content depends partly on whether the active compound is present in liquid or solid form, and which granulating auxiliaries, fillers, etc. are used.

In addition, the stated active compound formulations may contain the particular conventional adhesives, wetting agents, dispersants, emulsifiers, penetration agents, solvents, fillers or carriers.

For use, the concentrates present in the commercial form are, if appropriate, diluted in a conventional manner, for example, for wettable powders, emulsifiable concentrates and dispersions, and in some cases also for microgranules, by means of water. Dust-like and granulated formulations and atomizable solutions are not usually diluted with further inert substances before use.

Mixtures or mixed formulations with other active compounds, such as, for example, insecticides, acaricides, herbicides, fertilizers, growth regulators or other fungicides may be possible, and in certain circumstances it may also be possible to achieve synergistic increases in actions.

A few formulation examples are listed below:

A dusting agent is obtained by mixing 10 parts by weight of active compound and 90 parts by weight of talc as an inert substance, and comminuting the mixture in a hammer mill.

A wettable powder which is readily dispersible in water is obtained by mixing 25 parts by weight of active compound, 64 parts by weight of kaolin-containing quartz as an inert substance, and 10 parts by weight of potassium ligninsulfonate and 1 part by weight of sodium oleoylmethyltaurinate as a wetting agent and a dispersant, and milling the mixture in a pinned disc mill.

A dispersion concentrate which is readily dispersible in water is produced by mixing 20 parts by weight of active compound with 6 parts by weight of alkylphenol polyglycol ether (Triton X 207), 3 parts by weight of isotridecanol polyglycol ether (8 ethylene oxide units) and 71 parts by weight of paraffinic mineral oil (boiling range, for example, about 255° to above 377° C.), and milling the mixture to a fineness of below 5 microns in a frictional ball mill.

An emulsifiable concentrate can be produced from 15 parts by weight of active compound, 75 parts by weight of cyclohexanone as a solvent, and 10 parts by weight of oxyethylated nonylphenol (10 ethylene oxide units) as an emulsifier.

The examples which follow serve to illustrate the invention further.

A. PREPARATION EXAMPLES

EXAMPLE I

1-Chloro-1,2-diphenyl-3-(1,2,4-triazol-1-yl)-prop-1-ene 26.3 g (0.1 mole) of 1,3-dichloro-1,2-diphenylprop-1-ene are added to a mixture of 7.59 g (0.11 mole) of 1,2,4-triazole and 15.2 g (0.11 mole) of potassium carbonate in 70 ml of dimethylformamide at room temperature. The temperature increases to 44° C., and the mixture is stirred for a further 3 hours at 50° C., after which it is poured onto ice and extracted by shaking with dichloromethane. After the solvent has been distilled off, 27.2 g (92%) of a colorless substance of melting point 123°–4° C. remains. $C_{17}H_{14}ClN_3$ (295.5)

calculated: C: 69.0, H: 4.7, N: 14.2, found: C: 68.3, H: 4.8, N: 14.1.

IR (KBr): 3115, 3040 (CH), 1500, 1440, 1335, 1270, 1200, 1130, 1015, 890, 850, 780, 760, 745, 720, 680, 670, 650, 630 cm$^{-1}$.

NMR (CDCl$_3$): =4.95 (s, 2H, CH$_2$—), 7.00–7.60 (m, 12H, pH+triazole).

EXAMPLES 2 TO 28

Using the compounds below, other 3-azolyl-1,2-diaryl-1-halogenoprop-1-enes were prepared according to the method described in Example 1.

In all compounds of the formula (II) which were employed, Hal was chlorine, except in the case of the compound used for Example 11, where Hal denoted bromine.

| Example No. | Starting materials 1,2-Diaryl-1,3-dihalogenoprop-1-ene of the formula (II) | | | | Azole[1] | Product of the process melting point or boiling point (°C.) |
|---|---|---|---|---|---|---|
| | $(R^1)_n$ | $(R^2)_m$ | $R^3$ | $R^4$ | | |
| 2 | H | H | H | Cl | Im | 132-4 |
| 3 | H | H | H | Br | Tr | 98-105 |
| 4 | H | H | H | Br | Im | 195/0.03 |
| 5 | 4-CH$_3$ | H | H | Cl | Tr | 191-3/0.01 |
| 6 | 4-CH$_3$ | H | H | Cl | Im | 200-2/0.008 |
| 7 | 4-Cl | H | H | Cl | Tr | oil |
| 8 | 4-Cl | H | H | Cl | Tr | 127-8[2] |
| 9 | 4-Cl | H | H | Cl | Im | oil |
| 10 | H | 4-Cl | H | Cl | Tr | 198-200/0.03 |
| 11 | H | 4-Cl | H | Cl | Im | 212-4/0.03 |
| 12 | 4-Cl | 4-Cl | H | Cl | Tr | oil |
| 13 | 4-Cl | 4-Cl | H | Cl | Im | oil |
| 14 | 4-CH$_3$ | 4-Cl | H | Cl | Tr | 260 (decomposition)[3] |
| 15 | 4-CH$_3$ | 4-Cl | H | Cl | Im | 217 (decomposition)[3] |
| 16 | 4-CH$_3$ | 4-Cl | H | Cl | Im | 60-2 |
| 17 | 2,4-(CH$_3$)$_2$ | 4-Cl | H | Cl | Tr | 259 (decomposition)[3] |
| 18 | 2,4-(CH$_3$)$_2$ | 4-Cl | H | Cl | Im | 211 (decomposition)[3] |
| 19 | H | 3-Cl | H | Cl | Tr | oil |
| 20 | H | 4-OCH$_3$ | H | Cl | Tr | oil |
| 21 | 2,4-(CH$_3$)$_2$ | 3,4-(OCH$_3$)$_2$ | H | Cl | Tr | oil |
| 22 | H | 2,4-Cl$_2$ | H | Cl | Tr | 85-8 |
| 23 | H | 2,4-Cl$_2$ | H | Cl | Im | oil |
| 24 | H | 3,4-Cl$_2$ | H | Cl | Tr | 221-3/0.05 |
| 25 | H | 3,4-Cl$_2$ | H | Cl | Im | 232/0.04 |
| 26 | 4-CH$_3$ | 3,4-Cl$_2$ | H | Cl | Tr | 272 (decomposition)[3] |
| 27 | 4-CH$_3$ | 3,4-Cl$_2$ | H | Cl | Im | 258 (decomposition)[3] |
| 28 | H | H | CH$_3$ | Cl | Tr | oil |
| 29 | 4-CH$_3$ | 4-Cl | H | Cl | Pyr | 200-8/0.015 |
| 30 | H | 2-Br, 4-Cl | H | Cl | Tr | oil |
| 31 | H | 2-Br, 4-Cl | H | Cl | Tr | 79 (decomposition)[4] |
| 32 | H | 2-F | H | Cl | Tr | oil |

[1] Im = imidazole; Tr = triazole; Pyr = pyrazole
[2] as the nitrate
[3] as a salt with ½ naphthalene-1,5-disulfonic acid
[4] as a complex with ½ CuCl$_2$.

B. BIOLOGICAL EXAMPLES

EXAMPLE I

Wheat plants in the 3-leaf stage are inoculated to a pronounced extent with conidia of powdery mildew of wheat (Erysiphe graminis), and are placed in a greenhouse at 20° C. and a relative atmospheric humidity of 90 to 95%. 3 days after inoculation, the plants are sprayed, until dripping wet, with the compounds to be tested, in active compound concentrations of 500, 250, 125, 60, 30 and 15 mg/liter of spray liquor. After an incubation period of 10 days, the plants are examined for infestation by powdery mildew of wheat.

The degree of infestation is expressed as a percentage of infested leaf area, relative to untreated, infected control plants (=100% infestation). The results are shown in Table I below.

TABLE I

| Compound according to Example No. | Leaf area infested with powdery mildew of wheat, in % in the case of . . . mg of active compound/liter of spray liquor | | | | | |
|---|---|---|---|---|---|---|
| | 500 | 250 | 125 | 60 | 30 | 15 |
| 1 | 0 | 0 | 0 | 0 | 0 | 0 |
| 5 | 0 | 0 | 0 | 0 | 0 | 0-3 |
| 7 | 0 | 0 | 0 | 0 | 0 | 0-3 |
| 8 | 0 | 0 | 0 | 0 | 0 | 0 |
| 22 | 0 | 0 | 0 | 0 | 0 | 0 |
| 10 | 0 | 0 | 0 | 0 | 0 | 0 |
| 11 | 0 | 0 | 0 | 0 | 0 | 0 |
| 12 | 0 | 0 | 0 | 0 | 0 | 0 |
| 2 | 0 | 0 | 0 | 0 | 0 | 0-3 |
| Untreated, infected plants | | | 100 | | | |

EXAMPLE II

Barley plants in the 3-leaf stage are inoculated to a pronounced extent with conidia of powdery mildew of barley (Erysiphe graminis sp. hordei), and are placed in a greenhouse at 20° C. and a relative atmospheric humidity of 95 to 95%. 3 days after inoculation, the plants are sprayed, until dripping wet, with the compounds to be tested, in active compound concentrations of 500, 250, 125, 60 and 30 mg/liter of spray liquor. After an incubation period of 10 days, the plants are examined for infestation by powdery mildew of barley. The degree of infestation is expressed as a percentage of infested leaf area, relative to untreated, infected control plants (=100% infestation). The results are shown in Table II.

TABLE II

| Compound according to Example No. | Leaf area infested with powdery mildew of barley, in %, in the case of . . . mg of active compound/liter of spray liquor | | | | |
|---|---|---|---|---|---|
| | 500 | 250 | 125 | 60 | 30 |
| 1 | 0 | 0 | 0 | 0 | 0 |
| 5 | 0 | 0 | 0 | 0 | 0 |
| 7 | 0 | 0 | 0 | 0 | 0 |
| 8 | 0 | 0 | 0 | 0 | 0 |
| 22 | 0 | 0 | 0 | 0 | 0 |
| 10 | 0 | 0 | 0 | 0 | 0 |
| 11 | 0 | 0 | 0 | 0 | 0 |
| 12 | 0 | 0 | 0 | 0 | 0 |
| 2 | 0 | 0 | 0 | 0 | 0 |
| Untreated, infected plants | | | 100 | | |

EXAMPLE III

Cucumber plants (Delicatess variety) in the 2-leaf stage are inoculated to a pronounced extent with a conidia suspension of powdery mildew of cucumber (Erysiphe cichoracearum). After a period of 30 minutes in which the spore suspension dries on, the plants are placed in a greenhouse at 22° C. and 90% relative atmospheric humidity. 3 days after infection, the plants are sprayed, until dripping wet, with the compounds to be tested, in the active compound concentrations given in Table III. Assessment is carried out after 10 days. The degree of infestation is expressed as a percentage of the infested leaf area, relative to untreated, infected control plants (=100% infestation). The results are shown in Table III.

TABLE III

| Compound according to Example No. | Leaf area infested with powdery mildew of cucumber, in %, in the case of . . . mg of active compound/liter of spray liquor | | | | |
|---|---|---|---|---|---|
| | 500 | 250 | 125 | 60 | 30 |
| 1 | 0 | 0 | 0 | 0 | 0 |
| 5 | 0 | 0 | 0 | 0 | 0-3 |
| 7 | 0 | 0 | 0 | 0 | 0-3 |
| 8 | 0 | 0 | 0 | 0 | 0-3 |
| 22 | 0 | 0 | 0 | 0 | 0 |
| 10 | 0 | 0 | 0 | 0 | 0 |
| 11 | 0 | 0 | 0 | 0 | 0 |
| 12 | 0 | 0 | 0 | 0 | 0 |
| 2 | 0 | 0 | 0 | 0 | 0 |
| Untreated, infected plants | | | 100 | | |

EXAMPLE IV

Apple stock of the EM IX variety, in the 4-leaf stage, are infected to a pronounced extent with a conidia suspension of powdery mildew of apple (Podosphaera leucotricha). The plants are then placed in a climatically controlled chamber at 20° C. and a relative atmospheric humidity of about 100% for 16 hours. Thereafter, they are placed in a greenhouse at 22° C. and a relative atmospheric humidity of 85%. 3 days after infection, the plants are sprayed, until dripping wet, with the compounds to be tested, in the active compound concentrations mentioned in Table IV. After 2 to 3 weeks, the infestation with powdery mildew is assessed, and the degree of infestation is expressed as a percentage of the infested leaf area, relative to untreated, infected control plants (=100% infestation). The results are summarized in Table IV.

TABLE IV

| Compound according to Example No. | Leaf area infested with powdery mildew of apple, in %, in the case of . . . mg of active compound/liter of spray liquor | | | | |
|---|---|---|---|---|---|
| | 500 | 250 | 125 | 60 | 30 |
| 7 | 0 | 0 | 0 | 0 | 0 |
| 22 | 0 | 0 | 0 | 0 | 0 |
| 10 | 0 | 0 | 0 | 0 | 0 |
| 12 | 0 | 0 | 0 | 0 | 0 |
| Untreated, infected plants | | | 100 | | |

EXAMPLE V

Apple stock (EM IX) in the 4-leaf stage are sprayed, until dripping wet, with the compounds to be tested, in the use concentrations of 500, 250, 125 and 60 mg of active compound/liter of spray liquor. After the coating of active compound had dried on, the plants were infected to a pronounced extent with conidia of apple scab (Venturia inaequalis), and were placed, while dripping wet, in a climatically controlled chamber whose temperature was 22° C. and whose relative atmospheric humidity was 100%. After a period of infection of 48 hours, the plants were placed in a greenhouse at 18° C. and a relative atmospheric humidity of 95 to 100%. After an incubation period of 14 days, the plants were examined for infestation with apple scab (Venturia inaequalis). The infestation was assessed by appearance, in the conventional manner. The degree of infestation was expressed as a percentage of infested leaf area, relative to untreated, infected plants, and is represented in Table V.

TABLE V

| Compound according to Example No. | % Scab infestation in the case of ... mg of active compound/liter of spray liquor | | | |
|---|---|---|---|---|
| | 500 | 250 | 125 | 60 |
| 1 | 0 | 0 | 0 | 0 |
| 22 | 0 | 0 | 0 | 0 |
| 10 | 0 | 0 | 0 | 0 |
| 11 | 0 | 0 | 0 | 0 |
| 12 | 0 | 0 | 0 | 0 |
| Untreated, infected plants | | 100 | | |

EXAMPLE VI

Sugar beet plants in the 6-leaf stage were treated with the compounds to be tested, in the use amounts of 500, 250, 125 and 60 mg/liter of spray liquor.

After the coating of active compound had dried on, the plants were inoculated to a pronounced extent with conidia of the causative organism of leaf spot disease of beet (Cercospora beticola), and were placed, while dripping wet, in a climatically controlled chamber at about 100% relative atmospheric humidity and at 25° C. 14 days later, they were examined for infestation with leaf spot disease. The degree of infestation was expressed as a percentage of infested leaf area, relative to untreated, infected control plants (=100%). The results are shown in Table VI.

TABLE VI

| Compound according to Example No. | Leaf area infested with Cercospora beticola, in %, in the case of ... mg of active compound/liter of spray liquor | | | |
|---|---|---|---|---|
| | 500 | 250 | 125 | 60 |
| 1 | 0 | 0 | 0 | 0 |
| 22 | 0 | 0 | 0 | 0 |
| 10 | 0 | 0 | 0 | 0 |
| 12 | 0 | 0 | 0 | 0-3 |
| Untreated, infected plants | | 100 | | |

EXAMPLE VII

Wheat plants were treated with the compounds to be tested, in the use concentrations mentioned in Table VII. After the coating of active compound had dried on, the plants were inoculated with spores of brown rust of wheat (Puccinia triticina), and were placed, while dripping wet, in a climatically controlled chamber at 20° C. and 100% relative atmospheric humidity. 24 hours later, the plants were again placed in a greenhouse, and 14 days after inoculation were examined here for infestation with brown rust of wheat. The degree of infestation was expressed as a percentage of infected leaf area, relative to untreated, infected control plants (=100% infestation). Table VII shows the good action of the compounds investigated.

TABLE VII

| Compound according to Example No. | % of leaf area infested with brown rust in the case of ... mg of active compound/liter of spray liquor | | | |
|---|---|---|---|---|
| | 500 | 250 | 125 | 60 |
| 6 | 0 | 0 | 0 | 0 |
| 22 | 0 | 0 | 0 | 0 |
| 10 | 0 | 0 | 0 | 0 |
| Untreated, infected plants | | 100 | | |

We claim:

1. A 3-azolyl-1,2-diaryl-1-halogenoprop-1-ene compound of the formula

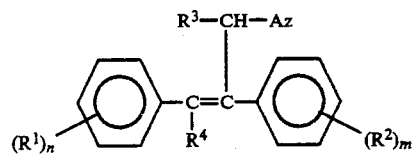

or a salt, complex salt, or quaternization product thereof, wherein n and m are 1, 2, or 3,
   all $R^1$ and $R^2$ are independently hydrogen, halogen, $-CF_3$, $-OCF_2CF_2H$, $C_1-C_8$-alkyl, $C_5$- or $C_6$-cycloalkyl, $C_1-C_6$-alkoxy, $C_2-C_6$-alkenoxy, phenoxy, phenyl or phenoxy or phenyl substituted by halogen.
   $R^3$ is hydrogen or $C_1-C_5$-alkyl,
   $R^4$ is chlorine or bromine, and
   Az is 1,2,4-triazol-1-yl.

2. A compound as in claim 1 which is 3-(1,2,4-triazol-1-yl)-1,2-diphenyl-1-chloroprop-1-ene.

3. A compound as in claim 1 which is 3-(1,2,4-triazol-1-yl)-2-(4-chlorophenyl)-1-phenyl-1-chloroprop-1-ene.

4. A compound as in claim 1 which is 3-(1,2,4-triazol-1-yl)-2-(2,4-chlorophenyl)-1-phenyl-1-chloroprop-1-ene.

5. A fungicidal composition comprising a fungicidally effective amount of a compound as in claim 1 and a carrier for said compound.

6. A method for combating fungi in plants which comprises applying to said plants a fungicidally effective amount of a compound as in claim 1.

* * * * *